(12) United States Patent
Heinonen

(10) Patent No.: US 6,681,643 B2
(45) Date of Patent: Jan. 27, 2004

(54) METHOD AND APPARATUS FOR DETERMINING A ZERO GAS FLOW STATE IN A BIDIRECTIONAL GAS FLOW CONDUIT

(75) Inventor: Erkki Heinonen, Helsinki (FI)

(73) Assignee: Instrumentarium Corp., Helsinki (FI)

( * ) Notice: Subject to any disclaimer, the term of this patent is extended or adjusted under 35 U.S.C. 154(b) by 0 days.

(21) Appl. No.: 10/062,175

(22) Filed: Jan. 31, 2002

(65) Prior Publication Data

US 2002/0116994 A1 Aug. 29, 2002

(30) Foreign Application Priority Data

Feb. 1, 2001 (EP) .............................. 01300924

(51) Int. Cl.⁷ ................................ G01F 1/22
(52) U.S. Cl. ................ 73/861.52; 73/204.11; 600/538
(58) Field of Search .............. 73/196, 204.11, 73/861.42, 861.52; 128/204.12–204.23; 600/538, 532

(56) References Cited

U.S. PATENT DOCUMENTS 3,903,876 A * 9/1975 Harris ........................ 600/537
4,036,217 A 7/1977 Ito et al. ..................... 600/536
5,088,332 A 2/1992 Merilainen et al. ...... 73/861.65
6,099,481 A 8/2000 Daniels et al. .............. 600/538

FOREIGN PATENT DOCUMENTS

EP 1004325 5/2000

* cited by examiner

*Primary Examiner*—Harshad Patel
(74) *Attorney, Agent, or Firm*—Andrus, Sceales, Starke & Sawall, LLP

(57) ABSTRACT

A method and apparatus for determining a state of zero gas flow in a conduit. A first gas flow signal has one polarity when gas flow is in one direction in the conduit and the opposite polarity when gas flow is in the opposite direction. A second gas flow signal has the same polarity for either direction of gas flow in the conduit. The derivatives of the first and second signals are taken at successive points in time to determine when the signs of the derivatives are present in a first predetermined combination of signs. A second point in time when the signs of the derivatives exhibit a second predetermined combination of signs different from the first combination is also determined. The combinations of signs are used to identify a state of zero gas flow in the conduit.

30 Claims, 5 Drawing Sheets

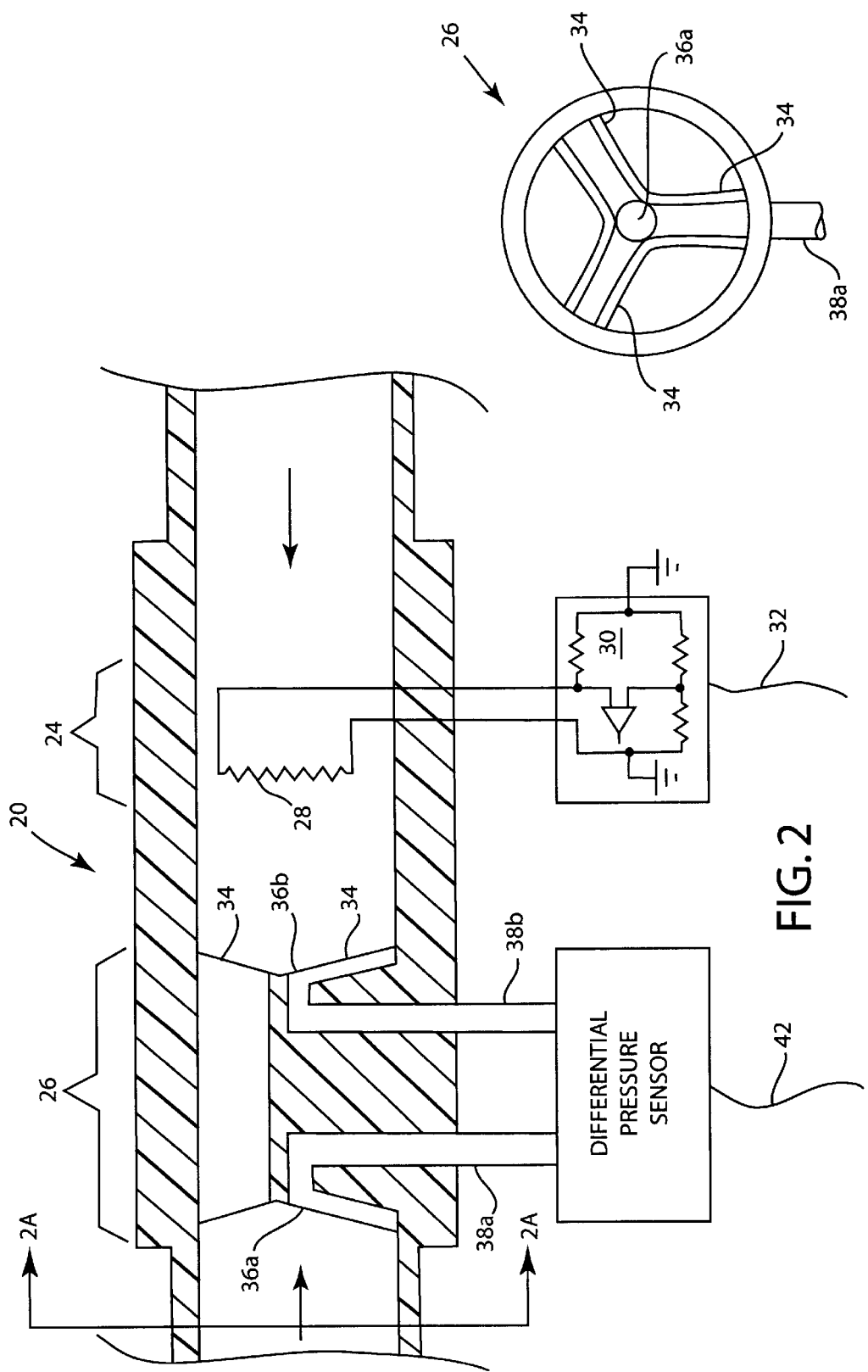

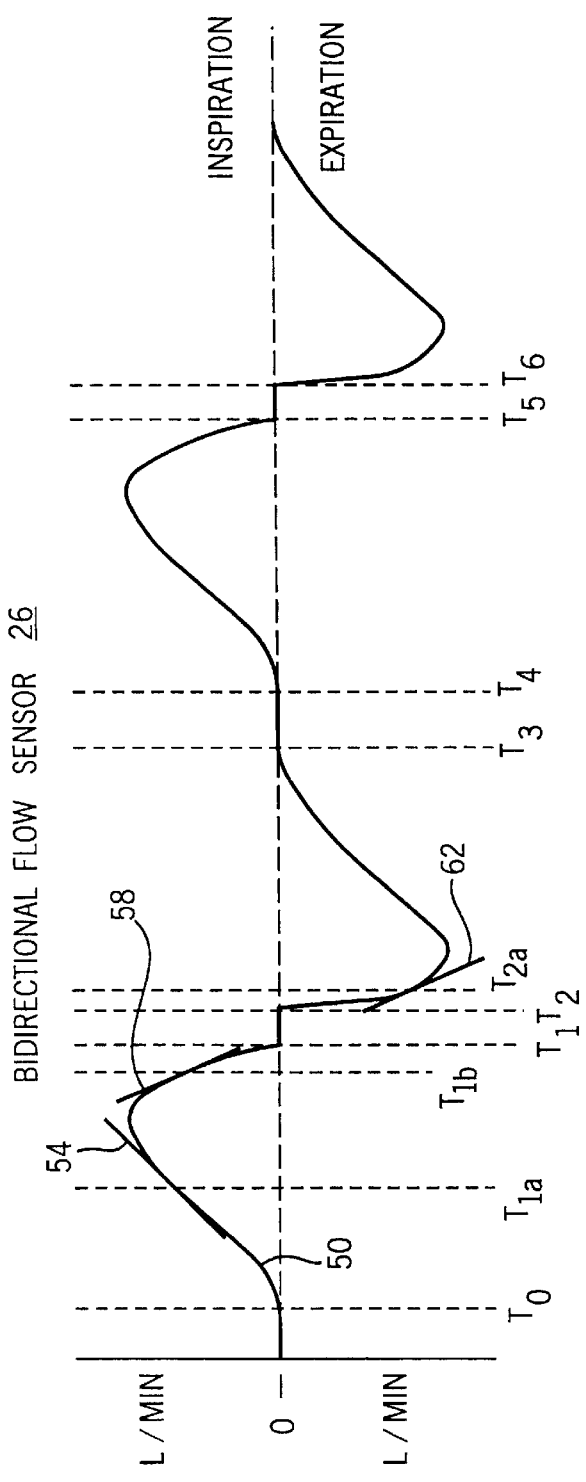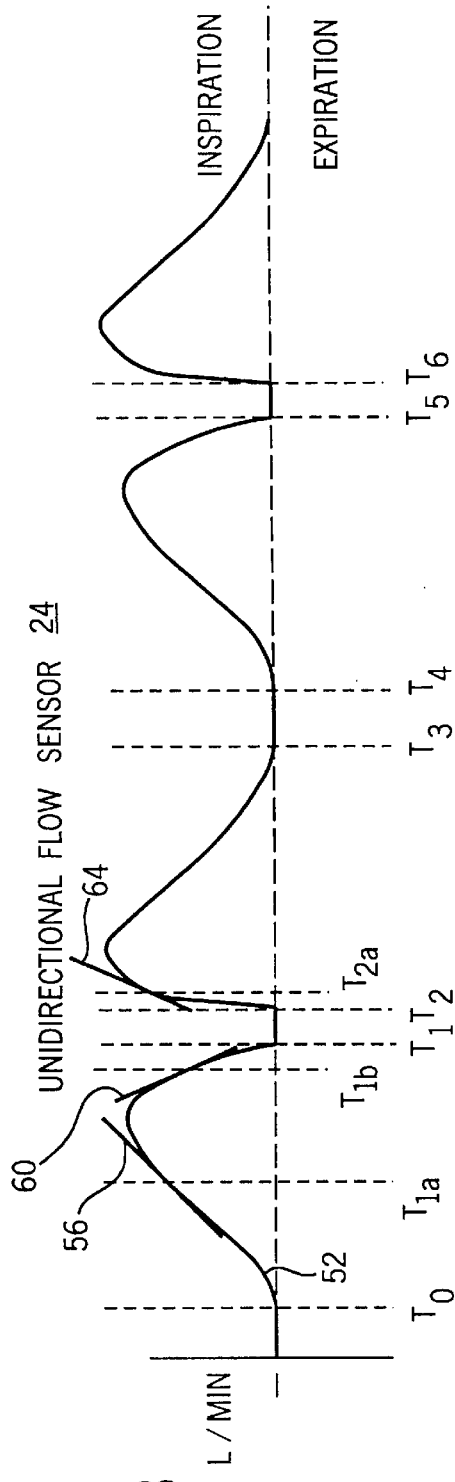
FIG. 3A
FIG. 3B

METHOD AND APPARATUS FOR DETERMINING A ZERO GAS FLOW STATE IN A BIDIRECTIONAL GAS FLOW CONDUIT

CROSS REFERENCE TO RELATED APPLICATION

The present application claims priority from European Patent Application No. 01300924.6, filed Feb. 1, 2001.

BACKGROUND OF THE INVENTION

The present invention is directed to a method and apparatus for determining a zero gas flow state in a conduit in which bidirectional gas flow occurs. In a typical application, the invention may be used to determine zero gas flow in the patient limb of a ventilator breathing circuit. Such a zero gas flow state occurs in the transition from inspiration to expiration, and vice versa. The output signals obtained from flow sensors in the patient limb when the zero gas flow state is present are used for calibrating the sensors.

During anaesthesia and in intensive care, patients are commonly connected to a ventilator having a breathing circuit that provides breathing gases to/from the patient. The breathing circuit includes an inspiratory, or inhalation, limb, one end of which is connected to the ventilator. The other end of the inspiratory limb is connected to one arm of a Y-piece connector. A second arm of the Y-piece connector is connected to the patient limb of the breathing circuit for supplying breathing gases to the patient through a face mask, endotracheal tube, or other suitable appliance. The third arm of the Y-piece connector is connected to one end of the expiratory, or exhalation, limb of the breathing circuit. The other end of the expiratory limb is connected to the ventilator.

During inspiration, the expiration limb of the breathing circuit is closed by an expiration valve of the ventilator and, in spontaneous breathing, the underpressure generated by the patient's lungs draws breathing gases from the inspiratory limb through the Y-piece connector to the patient limb and into the lungs. In artificial ventilation, the ventilator provides an overpressure in the breathing circuit that supplies the breathing gases into the lungs of the patient. During expiration, the expiration valve in the ventilator or breathing circuit is opened and the contraction of the patient's rib cage forces breathing gases through the patient limb and Y-piece connector into the expiration limb of the breathing circuit for discharge from the ventilator. The process is repeated on the next breath.

During each breath, bidirectional gas flow occurs in the patient limb of the breathing circuit. The breathing gases flow first in one direction into the lungs of the patient during the inspiratory phase of the respiratory cycle. Thereafter, at least an instant of zero gas flow occurs in the patient limb during a transition between inspiration and expiration. During expiration phase of the respiratory cycle, breathing gases flow in the opposite direction through the patient limb of the breathing circuit from the patient to the ventilator.

Gas flow rates in the breathing circuit can vary over a relatively wide range in the course of respiration, among patients of different ages, and with differing patient pulmonary conditions.

In one type of flow sensor commonly used to measure breathing gas flow rates, a flow restricting element is placed in the patient limb or other conduit. A pressure drop proportional to the gas flow rate is generated across the flow restrictor. Gas pressure sensing ports may be provided upstream and downstream of the flow restricting element and the pressure drop across the restrictor is measured by a differential pressure sensor. The differential pressure sensor can also determine, from the relative magnitudes of the pressures used in measuring the pressure drop, the direction of gas flow in the conduit.

Depending on the configuration of the flow sensor, the relationship of the magnitude of the pressure drop to gas flow rate may vary from that expressed by a linear relationship to one in which the pressure drop varies exponentially, for example, as the square of the gas flow rate.

While use of a flow sensor with a linear gas flow rate-output signal relationship simplifies gas flow sensing, it requires laminar flow conditions in the restrictor. This, in turn, necessitates the use of a plurality of finely structured flow channels in the flow restrictor to obtain the pressure drop. For applications such as measuring the flow rate of breathing gases, the finely structured flow channels may become blocked by mucus or other excretions from the lungs of the patient.

These difficulties have led to the use of flow restrictors in which the output signal varies as the square or some other exponent of the gas flow rate. While such sensors work well at high gas flows, the output signal is very small at low flows. This makes highly accurate gas flow measurements at low gas flow rates difficult. To obtain highly accurate measurements at low flows, it is necessary to obtain the sensor output signal at a zero gas flow condition in order to calibrate the sensor to remove errors that adversely effect low flow measurement.

To obtain the flow sensor output signal at zero gas flow conditions, the differential ports of the sensor can be temporarily short circuited, as for example, by means of a solenoid valve. However, during such a procedure, the measured gas flow rate output from the sensor is not available for patient monitoring purposes. This may limit the frequency with which calibration procedures can be carried out. But, errors or drift may arise in the sensor if the sensor calibrated too infrequently.

Also, the solenoid valve adds to the bulk of the gas flow sensor. Since the gas flow sensor is located in the patient limb, this can be a serious problem as the space around the patient's head may be crowded with other equipment. While elements of the flow sensor can be located remotely from the patient limb gas flow path, to transport the signals from the gas ports in the flow restrictor to the remote elements requires a double lumen, relatively large dimension tubing. This does not totally relieve congestion at the patient.

Another type of gas flow sensor is the so-called "hot wire" anemometer. In such an anemometer, a thin resistive wire is placed across the gas flow conduit so that the gas flows over the wire. The wire forms one arm of a Wheatstone bridge circuit. Energization of the bridge circuit passes current through the resistive wire increasing its temperature and causing it to become a "hot wire." The resistance of the wire is proportional to its temperature. The flow of the gas past the hot wire carries off heat from the wire, altering its resistance in accordance with the amount of gas flow. To determine the amount of gas flow, the amount of current necessary to restore the hot wire to the original temperature may be used as an indication of the amount of gas flow. Or, the energization of the bridge may be kept constant, and the alteration in the resistance of the wire as its temperature is reduced, as reflected in the resulting imbalance in the bridge, can be used to determine the gas flow rate. While the anemometer has been described as using a wire, it can also be formed using a film.

However, in its simplest embodiment, a hot wire anemometer is not a direction sensitive flow sensor. Further, a major problem with such a flow sensor is that the only way to calibrate the hot wire anemometer at the zero flow condition is to stop the flow of gas in the conduit. In applications such as a breathing circuit for a patient, this creates significant, practical problems.

BRIEF SUMMARY OF THE INVENTION

It is, therefore, an object of the present invention to provide a method and apparatus by which the zero gas flow state in a bidirectional gas flow conduit can be determined using a flow sensing device having a pair of flow sensors. Determination of the zero gas flow state enables the device to be calibrated using zero gas flow offsets, thereby to provide accurate gas flow rate measurements over a wide range of flow rates, including low flow rates.

The present invention can be used in a patient breathing circuit and can accomplish the foregoing and other objects without altering the operation of the breathing circuit and without the need for the additional components, such as solenoid valves, closely associated with the flow sensors or patient limb of the breathing circuit, that have heretofore rendered flow sensor devices more difficult to use.

Briefly, in the present invention, a first signal responsive to the gas flow in conduit is obtained using a bidirectional flow sensor. The first signal has one polarity when the gas flow is in one direction in the conduit and the opposite polarity when the gas flow is in the opposite direction. A second gas flow signal is obtained using a uni-directional flow sensor, the output signal of which has the same polarity for either direction of gas flow in the conduit.

The derivatives of the first and second signals are obtained at successive points in time during gas flow in the conduit, for example that occurring during inspiration or expiration by the patient. The derivatives describe the instantaneous changes of the signals with respect to time. Whether the changes increase or decrease the output signals is indicated by the signs of the derivatives, i.e., as plus or minus signs.

During an inspiration or expiration phase of the respiratory cycle, the signs of the derivatives of the first and second signals will be present in a first predetermined combination of signs.

At the end of an inspiration or expiration, there will be a period of at least momentary zero gas flow during the transition to the subsequent phase of the respiratory cycle. The output signals from the sensors will ideally also be zero but, as a practical matter, will usually provide some output signal.

As respiration continues, the signs of the derivatives of the first and second signals are examined to detect changes in the signs. If, for example, the sign of the first signal derivative (bi-directional flow sensor) is unchanged, whereas the sign of the second signal derivative (unidirectional flow sensor) has changed, this indicates that a zero gas flow condition has occurred at the point in time when the sign of the second signal derivative changed. Alternatively, the zero gas flow may produce a zero slope derivative, i.e., one with no sign in one or both the signals and the period during which this occurs may be taken as one of zero gas flow.

The output signals from the sensors obtained in the zero gas flow state may be used to calibrate the flow sensors to obtain accurate gas flow rate measurements from the sensors.

Noise in the output signals may be filtered out or appropriate signal thresholds employed to facilitate determining the zero gas flow state.

Various other features, objects, and advantages of the invention will be made apparent from the following detailed description and the accompanying drawing.

BRIEF DESCRIPTION OF THE SEVERAL VIEWS OF THE DRAWING

In the drawing:

FIG. 2 is a detailed view of a flow sensor device of the present invention suitable for use in the breathing circuit shown in FIG. 1;

FIG. 2A is a cross sectional view taken along the line 2A—2A of FIG. 2;

FIGS. 3A and 3B are graphs showing, in simplified, exemplary form, flow sensor output signals during the inspiratory and expiratory phases of a respiratory cycle of a patient and showing certain principles employed in the method and apparatus of the present invention.

DETAILED DESCRIPTION OF THE INVENTION

Figure 1:
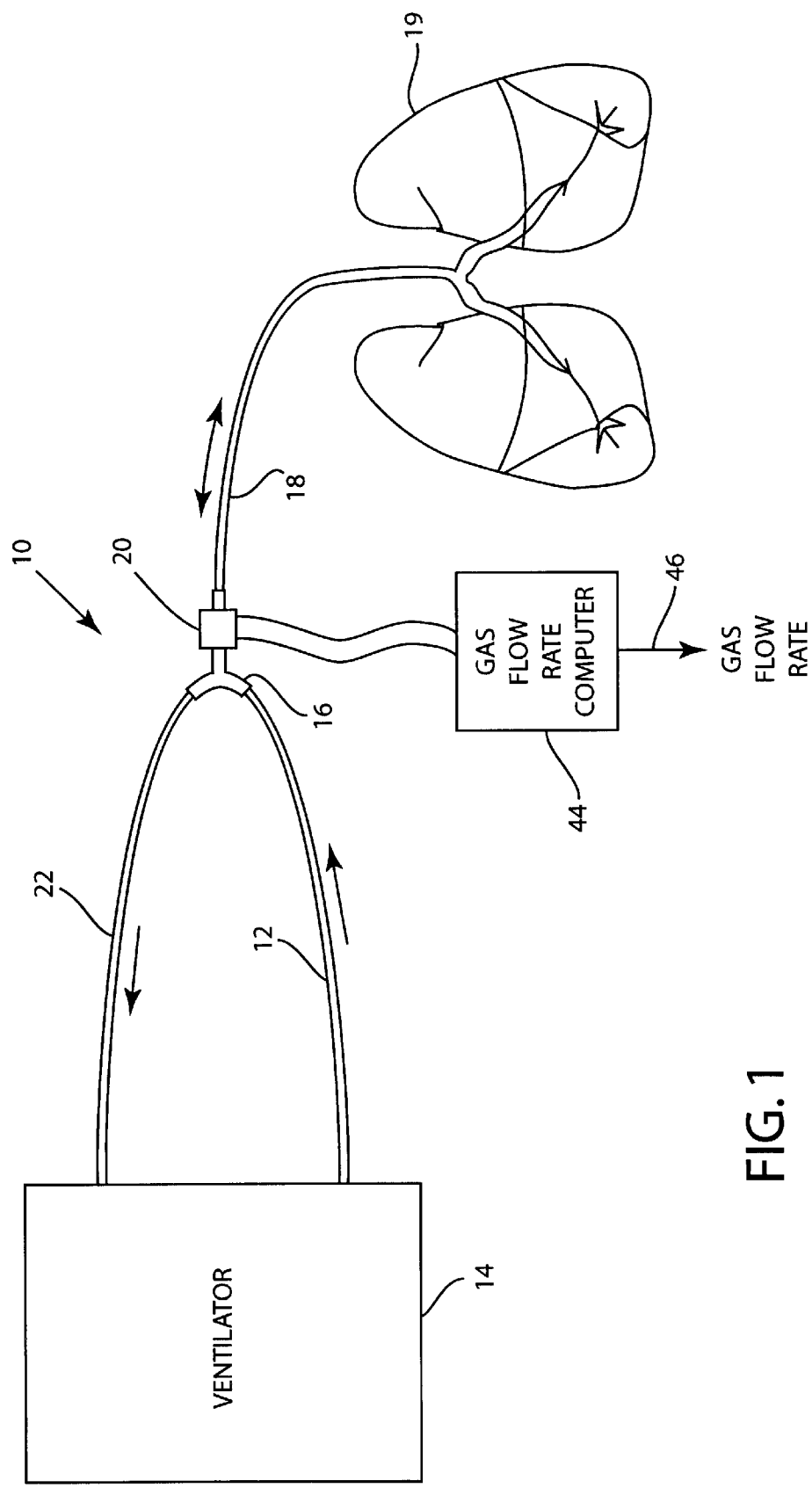
FIG. 1 is a general schematic view of a ventilator and breathing circuit with which the method and apparatus of the present invention may be used.

As shown in FIG. 1, breathing circuit 10 includes inspiratory limb 12. One end of inspiratory limb 12 is connected to ventilator 14. The other end of inspiratory limb 12 is connected to one arm of Y-piece connector 16. Another arm of Y-piece connector 16 is connected to patient limb 18 that supplies breathing gases to, and receives breathing gases from, the lungs 19 of a patient via a face mask, endotracheal tube, or other suitable appliance. Patient limb 18 contains flow sensing apparatus 20 for measuring breathing gas flows in the patient limb. Patient limb 18 may also include other components, not shown, such as a bacteria filter, heat and moisture filter, qualitative gas sampling means, and the like.

The third arm of Y-piece connector 16 is connected to one end of expiratory limb 22, the other end of which is connected to ventilator 14. Ventilator 14 supplies breathing gases to inspiratory limb 12 during the inspiratory phase of the respiratory cycle and receives breathing gases from expiratory limb 22 during the expiratory phase of the respiratory cycle.

FIG. 2 shows flow sensing apparatus 20, in detail. Flow sensing apparatus 20 includes series connected unidirectional flow sensor 24 and bidirectional flow sensor 26.

Unidirectional flow sensor 24 may comprise a flow sensor of the hot wire anemometer type, as schematically shown in FIG. 2. As noted above, hot wire anemometer 24 includes wire or film 28 inserted in patient limb 22 and subjected to the gas flow in the limb. Wire/film 28 is coupled to a bridge circuit 30, shown diagrammatically in FIG. 2, to provide a gas flow rate output signal in conductor 32.

Bidirectional flow sensor 26 may be of the type employing a flow restricting element that generates a pressure drop proportional to the flow in patient limb 18. Such a flow sensor is described in U.S. Pat. No. 5,088,332 and is shown in FIGS. 2 and 2A to include vanes or baffles 34 positioning opposing apertures 36a and 36b in patient limb 18. Tubes 38a and 38b connect apertures 36a and 36b to differential pressure sensor 40 which provides a gas flow rate output signal in conductor 42.

While flow sensors 24 and 26 are shown as separate components in FIG. 2, the flow sensors may be integrated into a single chip, solid state component using micromachining, thin film deposition, and other suitable techniques.

Conductors 32 and 42 are connected to gas flow rate computer 44, which may be comprised of a microprocessor. Gas flow rate computer employs the signals in conductors 32 and 42 to provide a gas flow rate output at 46. The signal processing carried out by computer 44 may include combining or selecting the signals from sensors 24 and 26, filtering or other signal noise reduction, time synchronizing the signals in conductors 32 and 42, carrying out the steps necessary to calibrate the sensors, and the like. The signals in conductors 32 and 42 may be digitized in order to carry out the signal processing.

Figure 4A:
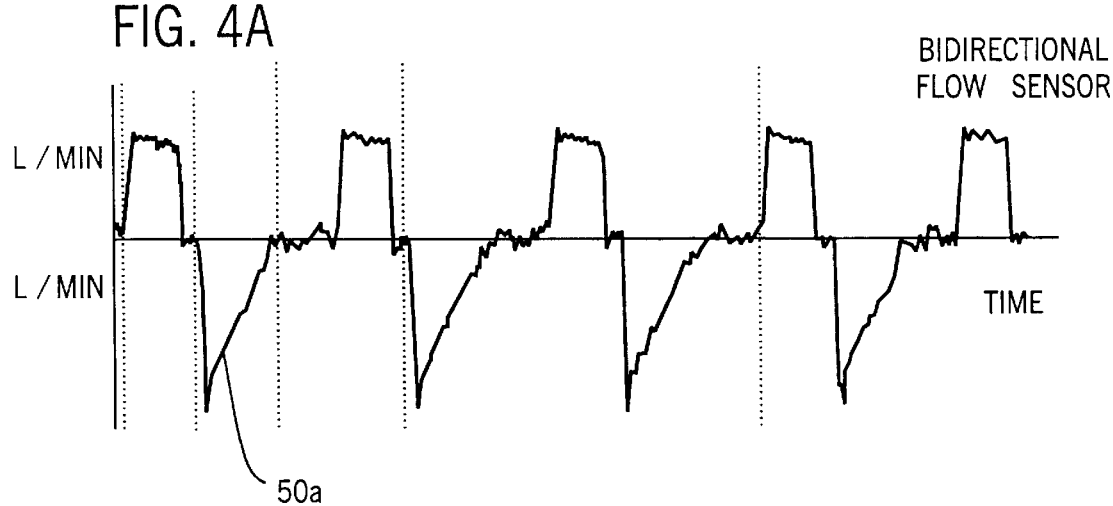
FIGS. 4A through 4E, are graphs showing typical output signals from flow sensors during inspiration and expiration and showing the detection of the zero gas flow state.
Figure 4B:
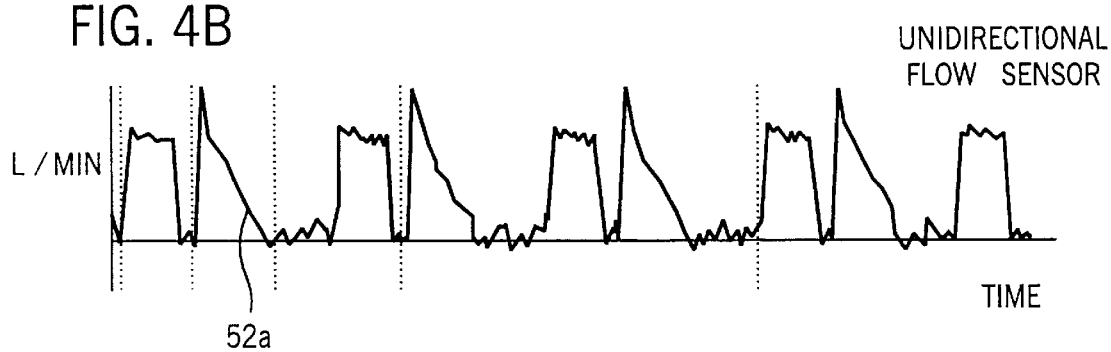

Typical output signals for flow sensors 24 and 26 are shown in simplified form in FIGS. 3A and 3B and in a more actual form in FIGS. 4A and 4B. FIG. 3 shows a case in which the patient is spontaneously breathing. FIG. 4 shows a case in which the patient is being mechanically ventilated.

FIG. 3A shows the output signal curve of bidirectional flow sensor 26 while FIG. 3B shows the output signal curve of unidirectional flow sensor 24. The abscissa of FIGS. 3 and 4 is a time scale. The ordinate of FIGS. 3A through 4B shows gas flow in liters per minute. An inspiratory phase of the respiratory cycle commences at time $T_0$ as breathing gas starts to flow into the lungs of patient 20. This flow of breathing gas is measured by flow sensors 26 and 24 as shown by graphs 50 and 52, respectively. As the lungs of patient 20 fill with breathing gas, the flow of breathing gas slows and stops at time $T_1$. There is then at least a momentary period of zero gas flow between the inspiratory phase and the expiratory phase in which there is no gas flow into or out of the lungs 20 of the patient. FIGS. 3A and 3B show this extending from time $T_1$ to time $T_2$. Thereafter, the expiratory phase commences at time $T_2$ as breathing gas starts to flow out of the lungs 20 of the patient. As the lungs empty of breathing gas, the flow of breathing gas again slows and stops at time $T_3$. There is another at least momentary period in which there is no gas flow into or out of the lungs of patient 20. FIGS. 3A and 3B show this extending from time $T_3$–$T_4$. Two zero gas flow states thus exist in each respiratory cycle of the patient: one corresponding to the transition from inspiration to expiration at time $T_1$–$T_2$ and the other corresponding to the transition from expiration to inspiration at time $T_3$–$T_4$. After time $T_4$, another inspiratory phase of the respiratory cycle commences and another zero gas flow period occurs at time $T_5$–$T_6$.

Since FIG. 3A shows the output signal curve 50 for bidirectional flow sensor 26, the output signal curve of the flow sensor during the inspiratory gas flow to the patient appears above the abscissa of the figure, whereas the output signal for gas flow in the opposite direction from the patient appears below the abscissa. For unidirectional flow sensor 24, which is not responsive to the direction of gas flow to or from the patient, the entire output signal curve 52 of the flow sensor appears above the abscissa as shown in FIG. 3B. For explanatory purposes, whether output signal curve is above or below the abscissa may be said to be described by the "polarity" of the signal. Thus, output signal curve 50 has bipolarity whereas output signal curve 52 is unipolar.

The same is true with respect to FIGS. 4A and 4B. These figures show mechanical ventilation of a patient in which breathing gases are provided to lungs 19 of the patient by an overpressure provided by ventilator 14. Thus, the shape of the output signal curve from sensors 26 and 24 for the inspiratory phase differs from that shown in FIGS. 3A and 3B. In the expiratory phase, the patient exhales in a natural manner so that the output signal curve for flow sensors 26 and 24 shown in FIGS. 4A and 4B more closely resembles that shown in simplified form in FIGS. 3A and 3B.

As noted above, the object of the present invention is to determine when a zero gas flow state exists in patient limb 18. This enables the zero gas flow output signals from flow sensors 24, 26 to be obtained so that the flow sensors can be calibrated, as by using the zero gas flow output signals so obtained as an offset to alter the output signals of the flow sensors to zero when there is zero gas flow in patient limb 18.

To carry out the method of the present invention, the derivatives of the output signal curves 50 and 52 of flow sensors 26 and 24 is obtained at successive points in time. As a mathematical concept, a derivative describes the instantaneous change of one quantity with respect to another quantity, for example, the instantaneous change in gas flow through a conduit with respect to time. For the graphic display of the output signal curves shown in FIGS. 3 and 4, the derivative of any point on the curves can be shown by a straight line tangent to the curve at the given point and the derivative is the slope, i.e. $\Delta y/\Delta x$, of the line, where y is the ordinate and x is the abscissa. Conventionally, the slope of tangent lines sloping upwardly to the right is said to have a positive or plus sign whereas the slope of tangent lines sloping downwardly to the right is said to have a negative or minus sign. The sign of the derivative thus reflects whether the change is one to increase the quantity or to decrease the quantity.

Lines tangent to the simplified flow sensor output signal curves 50, 52 of FIGS. 3A and 3B are shown in those figures. For the inspiratory phase extending between time $T_0$ and time $T_1$, since the output signal curves 50, 52 are both above the neutral axis, the slopes, and corresponding signs of the tangent lines and derivatives will be the same. That is, in the initial portion of the inspiratory phase containing point $T_{1a}$, the tangent lines 54, 56 shown in FIGS. 3A and 3B both slope upwardly to the right and have a positive or plus sign. As the curves of the output signals approach the end of the inspiratory phase at time $T_{1b}$, the tangent lines 58, 60 both slope downwardly and the derivatives of curves 50, 52 are both negative or minus. Gas flow rate computer 44 may be used to determine the derivatives of the curves and their slopes at successive points along the curves.

At time $T_1$, the inspiratory phase of the respiratory cycle ends and a period of zero gas flow in patient limb 18 occurs. This is seen by the horizontal line in the curves 50, 52 of the simplified showing of FIGS. 3A and 3B. The output signals may be displaced from the neutral axis since the output signals of sensors 26, 24 may not be zero for the zero gas flow state in patient limb 18. A tangent line illustrating the derivative of the output signal curves in time interval $T_1$–$T_2$, is a horizontal line coincidental with curves 50, 52 and thus has no slope or sign. As hereinafter noted, the $T_1$–$T_2$ time interval may actually be so momentary that a period during which the derivatives have no signs does not occur.

At time $T_2$, the exhalation phase of the respiratory cycle commences and the direction of gas flow in patient limb 18 reverses from that existing during the inspiratory phase.

FIGS. 3A and 3B show tangent lines 62 and 64 at time $T_{2a}$ on the output signal curves 50, 52 for flow sensors 26 and 24, respectively. It will be noted that tangent line 62, and the derivative of the output signal curve 50 in FIG. 3A continues to have a negative slope and sign, whereas tangent line 64 in FIG. 3B, and the associated derivative, now has a positive slope and sign.

The identification of the existence of a zero gas flow state in patient limb 18, such as that between times $T_1$ and $T_2$ or times $T_3$ and $T_4$, using the derivatives of the output signal curves of the flow sensors is carried out is as follows.

The identification may be commenced at a time when the derivative for the output signal curve 50 of flow sensor 26 and the derivative of the output signal curve 52 for flow sensor 24 have the same, negative or minus sign, as for example, in the latter stages of the inspiratory phase at time $T_{1b}$. Logic circuitry in gas flow rate computer 44 may be used to determine whether for successive points along curves 50, 52, the derivatives have signs and, if so, whether the signs are plus or minus, and whether the signs are the same or different.

Following the identification of a condition in which the derivatives of both curves are negative, it is thereafter noted when the derivative of output signal curve 52 for unidirectional flow sensor 24 becomes positive while the derivative of output signal curve 50 for bi-directional flow sensor 26 remains negative. The point in time at which the derivative of output signal curve 52 changes sign is one of zero gas flow. Or, a preceding point at which the derivatives of the output signal curves of flow sensors 24 and 26 have no sign may also be identified as a period of zero gas flow.

The output signals of flow sensors 24 and 26 when the zero gas flow state is detected are measured as zero flow offset signals for use in calibrating the flow sensors.

From a study of FIG. 3 it will be appreciated that similar phenomena occur before, during, and after the time period $T_3$–$T_4$ which characterizes the zero gas flow state transitory period between expiration and inspiration. The identification of this period is carried out by determining that the sign of the derivative output signal of curve 50 is positive, prior to time $T_3$, and the sign of the derivative of output signal curve 52 is negative. Subsequent to time $T_4$ the signs of the derivatives of both output signal curves are positive. The point in time at which the derivative of output signal curve 52 changes from negative to positive or the intervening period $T_3$–$T_4$ when the derivatives have no sign or slope is thus a period of zero gas flow. Offset signals may also be obtained during this period $T_3$–$T_4$ for use in calibrating the flow sensors.

Thus, if desired, the flow sensors may be calibrated as frequently as twice during each respiratory cycle of the patient with the method and apparatus of the present invention. As a practical matter, the flow sensors are usually calibrated less frequently. Also, it will be appreciated that the zero gas flow state is determined without interrupting the flow of gas in the conduit as was required with hot wire anemometers in the past.

FIG. 4 shows typical output signals 50a and 52a actually obtained from the flow sensors when a patient is provided with breathing gases from ventilator 14. As can be seen from FIGS. 4A and 4B, the actual output signals contain noise and other spurious phenomenon not shown in the simplified illustrations of FIG. 3. FIGS. 4C and 4D show the signal derivatives 150 and 152 of output signals 50a and 52a, respectively, obtained using a simplified derivation algorithm. When the graphs are above the neutral axis abscissa, they are deemed to have a plus sign. When they are below the neutral axis they are deemed to have a minus sign. The height of the graphic indicates the magnitude of the slope of the tangent line.

Figure 4C:
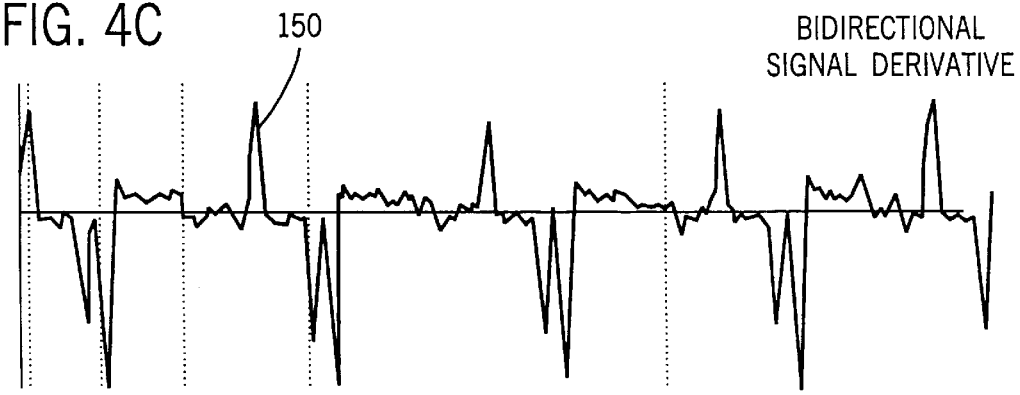
Figure 4D:
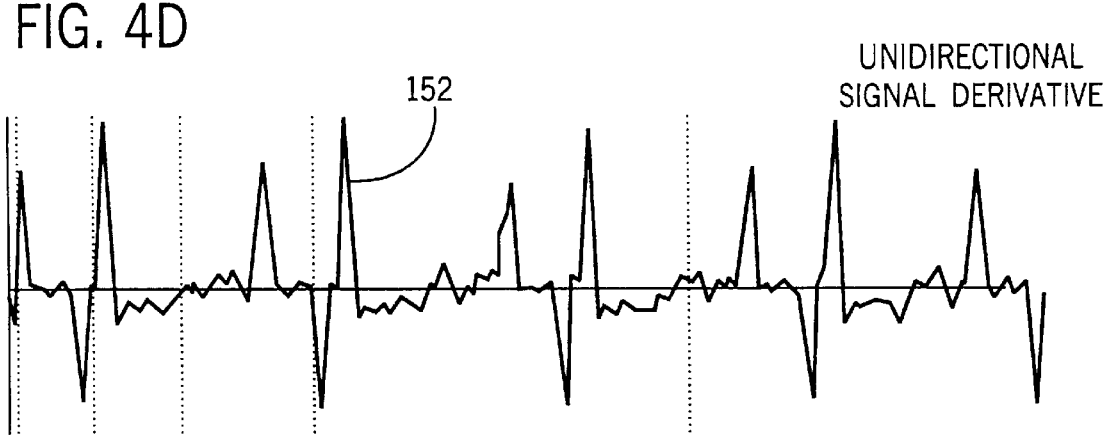
Figure 4E:

FIG. 4E shows the points at which zero gas flow are detected, also using a simplified algorithm for coincidence detection.

Thus, FIG. 4E shows a time interval $T_1$–$T_2$ which is analogous to that shown in FIG. 3. FIG. 4C shows that the sign of the derivative 150 of the bi-directional flow sensor output signal 50a remains negative as the transition from inspiration to expiration occurs, whereas the sign of the derivative 152 of the unidirectional flow sensor output signal 52a changes from negative to positive. The change indicates that a condition of zero gas flow has occurred in patient limb 18, as shown in FIG. 4E. Other points at which zero gas flow is detected are also shown in FIG. 4E.

While FIGS. 3 and 4 illustrate breathing patterns for the patient in which a transition from inspiration to expiration, or vice versa, can be seen, it will be appreciated that breathing patterns may occur in which the transition is only momentary. However, by determining that the sign of the unidirectional flow sensor output signal derivative 152 has changed but the sign of the derivative 150 of the bi-directional flow sensor output signal 50a has not changed indicates that a condition of zero gas flow occurred when the sign of derivative 152 changed.

For dealing with the effects of signal noise, use of an appropriate filter in the outputs of flow sensors 24 and 26 or in gas flow rate computer 44 or the use of signal thresholds in gas flow rate computer 44 for determining the zero gas flow state will facilitate correct identification of zero gas flow periods. Due to filtering, for example with the use of a filtering algorithm in computer 44, the resulting alterations to the sensor output signal derivatives may cause the zero gas flow condition not to be detected in some zero gas flow periods whereas in other such periods two or more zero gas flow conditions may be identified. FIGS. 4C and 4D show filtered sensor output signal derivatives.

Also, for purposes of explanation, FIG. 3 shows the output signal curves 50, 52 of sensors 24 and 26 as coincidentally measuring the gas flow in patient limb 18. However, flow sensors 24 and 26 are of different types in order to obtain complementary high flow rate-low flow rate measuring accuracy, to achieve unidirection and bi-unidirectional flow sensing, and for other reasons. There may therefore be differing response times, time delays, etc. in the flow sensors of different types so that one of the output signal curves may be time shifted along the abscissa of FIG. 3 with respect to the other output signal curve. To obtain the desired coincidence or synchronization in the output signal curves, compensation may be carried out in gas flow rate computer 44. Signal pattern recognition analysis, such as is commonly used in other biomedical applications, for example, electrocardiographic analysis, may be employed to identify time delays between the two output signals so that the comparisons of the signs of the derivatives of the output signal curves described above will be carried out at the same temporal points on the curves.

It is recognized that other equivalents, alternatives, and modifications aside from those expressly stated, are possible and within the scope of the appended claims.

What is claimed is:

1. A method for determining a state of zero gas flow in a conduit, the zero gas flow state occurring between a first period in which gas flows in one direction in the conduit and a subsequent, second period in which gas flows in the opposite direction in the conduit, said method comprising the steps of:

obtaining a first bipolarity signal indicative of the amount of gas flow in the conduit, the first signal having one polarity when the gas flow is in one direction in the conduit and the opposite polarity when the gas flow is in the opposite direction in the conduit;

obtaining a second unipolarity signal indicative of the amount of gas flow in the conduit, said second signal having the same polarity for either direction of gas flow in the conduit;

obtaining the derivatives of the first and second signals at successive points in dine;

determining that the signs of the derivatives of the first and second signals are present in a predetermined combination of signs;

when the derivatives have the first predetermined combination of signs, thereafter determining a first point in time at which the sign of the derivative of the second signal becomes opposite to its sign in the predetermined combination and the sign of the derivative of the first signal remains the same as its sign in the predetermined combination;

identifying a second point in time, prior to first point, as a state of zero gas flow in the conduit.

2. The method according to claim 1 wherein when the derivatives of first and second signals are present in the predetermined combination, the signs of the derivatives are the same.

3. The method according to claim 1 wherein when the derivatives of the first and second signals are present in the predetermined combination, the signs of the derivatives are different.

4. A method according to claim 1 further including the step of providing synchronization between said first and second output signals for obtaining the derivatives and identifying the first point.

5. The method according to claim 4 wherein the step of providing synchronization is further defined as carrying out pattern recognition analysis on said first and second signals.

6. The method according to claim 1 wherein said first and second signals contain noise and wherein said method includes the step of reducing or eliminating the effects of signal noise in the determination of the zero gas flow state.

7. The method according to claim 6 further including the step of filtering the first and second signals.

8. The method according to claim 6 further including the step of establishing a signal threshold in determining a state of zero gas flow in the conduit.

9. The method according to claim 1 wherein the first and second signals are obtained with flow sensors and wherein the method is further defined as including the step of measuring the outputs of the flow sensors in the zero gas flow state.

10. The method according to claim 9 further defined as one for calibrating the flow sensors and as including the step of calibrating the flow sensors using the zero gas flow state outputs of the flow sensors.

11. A method according to claim 1 further defined as a method for determining zero breathing gas flow in a patient limb of a breathing circuit.

12. The method according to claim 1 or 11 wherein the first and second signals are obtained with flow sensors and wherein the method is further defined as one for calibrating the flow sensors and as including the step of detecting the outputs of the flow sensors in the zero gas flow state and calibrating the flow sensors using the outputs.

13. The method according to claim 1 or 11 wherein the first and second signals are obtained with first and second gas flow sensors and wherein the gas flow sensors are of different types.

14. The method according to claim 13 wherein one of the gas flow sensors of the first and second gas flow sensors is a pressure operated gas flow sensor.

15. The method according to claim 13 wherein one of the gas flow sensors of the first and second gas flow sensors is a thermodynamic gas flow sensor.

16. The method according to claim 14 wherein the other of the first and second gas flow sensors is a thermodynamic gas flow sensor.

17. Apparatus for determining a state of zero gas flow in a conduit, the zero gas flow state occurring between a first period in which gas flows in one direction in the conduit and a subsequent, second period in which gas flows in the opposite direction in the conduit, said apparatus comprising:

a first gas flow sensor for obtaining a first signal indicative of the amount of gas flow in the conduit, the first signal having one polarity when the gas flow is in one direction in the conduit and the opposite polarity when the gas flow is in the opposite direction in the conduit;

a second gas flow sensor for obtaining a second signal indicative of the amount of gas flow in the conduit, said second signal having the same polarity for either direction of gas flow in the conduit;

means for obtaining the derivatives of the first and second signals at successive points in time and for determining their signs;

means for determining that the signs of the derivatives of the first and second signals are present in a predetermined combination of signs and thereafter determining a first point in time at which the sign of the derivative of the second signal becomes opposite to its sign in the predetermined combination and the sign of the derivative of the first signal remains the same as its sign in the predetermined combination, said means identifying a second point in time, prior to first point, as a state of zero gas flow in the conduit.

18. Apparatus according to claim 17 wherein said determining means is further defined as determining that when the derivatives of first and second signals are present in the predetermined combination, the signs of the derivatives are the same.

19. Apparatus according to claim 17 wherein said determining means is further defined as determining that when the derivatives of the first and second signals are present in the predetermined combination, the signs of the derivatives are different.

20. Apparatus according to claim 17 further including means for providing synchronization between said first and second output signals for obtaining the derivatives and identifying the first point.

21. Apparatus according to claim 20 wherein said synchronizing means is further defined as carrying out pattern recognition analysis on said first and second signals.

22. Apparatus according to claim 20 wherein said first and second signals contain noise and wherein said apparatus includes means for reducing or eliminating the effects of signal noise in the determination of the zero gas flow state.

23. Apparatus according to claim 22 further including filter for at least one of said first and second signals.

24. Apparatus according to claim 22 further including means for establishing a signal threshold determining a state of zero gas flow in the conduit.

25. Apparatus according to claim 17 wherein said apparatus further includes means for measuring the outputs of the flow sensors in the zero gas flow state.

26. Apparatus according to claim 17 further defined one for determining zero breathing gas flow in a patient limb of a breathing circuit.

27. Apparatus according to claim 17 wherein said first and second gas flow sensors are of different types.

28. Apparatus according to claim 27 wherein one of said gas flow sensors of the first and second gas flow sensors is a pressure operated gas flow sensor.

29. Apparatus according to claim 28 wherein one of the gas flow sensors of the first and second gas flow sensors is a thermodynamic gas flow sensor.

30. Apparatus according to claim 28 wherein the other of the first and second gas flow sensors is a thermodynamic gas flow sensor.

* * * * *